(12) United States Patent
Chiou

(10) Patent No.: US 7,258,875 B2
(45) Date of Patent: Aug. 21, 2007

(54) COMPOSITIONS AND METHODS FOR TOPICAL TREATMENT OF SKIN INFECTION

(75) Inventor: Win L. Chiou, Burr Ridge, IL (US)

(73) Assignee: Chiou Consulting, Inc., Burr Ridge, IL (US)

( * ) Notice: Subject to any disclaimer, the term of this patent is extended or adjusted under 35 U.S.C. 154(b) by 361 days.

(21) Appl. No.: 10/727,376

(22) Filed: Dec. 4, 2003

(65) Prior Publication Data

US 2005/0123620 A1   Jun. 9, 2005

(51) Int. Cl.
*A61K 31/28* (2006.01)
*A61K 33/32* (2006.01)
*A61K 33/24* (2006.01)

(52) U.S. Cl. ............ 424/641; 424/617; 424/639; 514/492

(58) Field of Classification Search ......... 424/639, 424/641, 647
See application file for complete search history.

(56) References Cited

U.S. PATENT DOCUMENTS

| | | | |
|---|---|---|---|
| 4,053,630 A * | 10/1977 | Yu et al. ............... | 514/502 |
| 4,224,339 A * | 9/1980 | Van Scott et al. ...... | 514/553 |
| 4,595,591 A * | 6/1986 | Mardi et al. ........... | 424/718 |
| 5,371,107 A * | 12/1994 | Hotzel et al. .......... | 514/474 |
| 5,567,716 A | 10/1996 | Della Valle et al. | |
| 5,667,790 A * | 9/1997 | Sellers, Jr. ............ | 424/401 |
| 5,851,556 A * | 12/1998 | Breton et al. .......... | 424/639 |
| 5,866,168 A * | 2/1999 | De Lacharriere et al. ... | 424/639 |
| 5,898,037 A * | 4/1999 | Marx .................... | 424/49 |
| 6,294,186 B1 | 9/2001 | Beerse et al. | |
| 6,372,784 B1 * | 4/2002 | Athanikar .............. | 514/503 |
| 6,599,525 B2 | 7/2003 | Scamilla Aledo et al. | |

OTHER PUBLICATIONS

Remington's Pharmaceutical Sciences, 18th ed., 1990, p. 768.*
Leyden, J. et al., "Erythromycin 2% gel in comparison with clindamycin phosphate 1% solution in acne vulgaris," *Journal of the American Academy of Dermatology*, vol. 16, No. 4, pp. 822-827 (Apr. 1987).
Odom, R. et al., "Chapter 13: Acne," *Andrews' Diseases of the Skin, Clinical Dermatology*, Ninth Edition, pp. 284-306 and 509-520 (2000).
Tierney, Jr., L. et al. (Editors), "Skin, Hair, & Nails," *2004 Lange: Current Medical Diagnosis & Treatment*, 43rd Edition, pp. 111-114 and 123-125 (2004).

* cited by examiner

*Primary Examiner*—San-Ming Hui
(74) *Attorney, Agent, or Firm*—Merchant & Gould

(57) ABSTRACT

The present invention describes an extremely effective, simple, novel, inexpensive, safe and quick method to treat both acne and warts, each with a different etiology and different clinical symptoms, by topically applying an effective amount of one or more polyvalent metal compounds. The polyvalent metal compounds include, but are not limited to, bismuth compounds, zinc compounds, magnesium compounds, aluminum compounds, calcium compounds, copper compounds, titanium compounds, manganese compounds, chromium compounds, barium compounds and iron compounds. The present invention can also be applied to the treatment of rosacea. The present invention can also be employed to prevent scarring and to facilitate healing or elimination of the scars once formed.

10 Claims, No Drawings

COMPOSITIONS AND METHODS FOR TOPICAL TREATMENT OF SKIN INFECTION

CROSS REFERENCE TO RELATED APPLICATIONS

This application is related to PCT International Application entitled "Compositions and Methods for the Prophylaxis and Treatment of Aphthous Ulcers and Herpes Simplex" filed on Jun. 7, 2002 with International Application No. PCT/US02/18223. No priority claim is made in this application.

FIELD OF THE INVENTION

The present invention relates to treating acne and warts with a topical application containing one or more polyvalent metal compounds, and also relates to prevention and healing or sloughing of scars on the skin.

BACKGROUND OF THE INVENTION

Skin infection is commonly treated with antimicrobial agents orally and/or topically. Topical treatment is preferred because it can minimize any potential systemic adverse effects of drugs and it is also less expensive. Acne, mainly caused by P. acnes, and warts (i.e., verruca) caused by human papillomavirus, are two common, potentially serious skin infectious diseases ("Current Medical Diagnosis and Treatment" by L. M. Tierney, Jr. et al., Lange Medical Books, NY, 2004, pp. 111-113 and 123-125; "Andrews' Diseases of the Skin, Clinical Dermatology" by R. B. Odom et al., Philadelphia, 2000, pp. 284-306 and 509-519.) Topical acne treatment commonly includes prescription-required antibiotics (such as erythromycin and clindamycin) and potent retinoids. The effectiveness of the above treatment method does not appear to be satisfactory since many weeks or months of continuous daily treatment are generally required. In one study, for example, only about 50% of patients showed satisfactory responses after 12 weeks of erythromycin or clindamycin treatment (J. J. Leyden, et al., J. Am. Acad. Dermatol. 1987; 16:822-827). Topical nonprescription drugs such as sulfur and salicylic acid are considered less effective. For topical treatment of warts, probably with the exception of salicylic acid, drugs such as bleomycin, 5-fluorouracil, podophyllin and imiquimod require a physician's prescription. Furthermore, at least two or three months of sustained treatment are generally required. Potential serious adverse effects of topical or systemic treatment for both acne and warts are well known. Furthermore, unsightly "permanent" scars are often present after completion of the treatment.

It is important to emphasize here that many reported antimicrobial compounds can kill the microorganisms and "cure" the diseases but often inhibit wound healing (U.S. Pat. No. 5,567,716 by Della Valle et al., Oct. 22, 1996). Furthermore, healing or treatment of a disease, a lesion or a wound may also result in the formation of an unsightly, undesirable scar on the skin ("Webster's New World Dictionary," edited by D. B. Garalnik, Prentice Hall Press, 1986, pp. 1271) as exemplified in the conventional treatment of acne, warts and herpes simplex.

The above brief review clearly indicates that there is an urgent need to develop a new, novel, simple, rapid, highly safe, highly effective topical treatment of acne and warts without leaving scars behind after the treatment. Ideally, the new drug treatment may not require a prescription, and the same drug can be used to treat both diseases. The present invention is aimed to achieve the above objectives.

SUMMARY OF THE INVENTION

The present invention relates to the surprising discovery that topical application of mixtures containing one or more polyvalent metal compounds can effectively heal the acne and warts in humans when applied from an appropriate dosage form. Thus, for example, for papular inflammatory acne, complete healing without any scars left behind (Examples I and II) was found in several subjects within one day after only one single application. For pustular inflammatory acne, virtually complete healing was found in just about one to two days of treatment (Examples I to III). For warts, a crust was formed and healing was found to begin shortly after one application. Near healing was found in about one week. A complete healing without any scar left was achieved in about two weeks. The speed of healing and the absence of permanent scars left (Examples I to IV) after topical administration of a composition of the present invention was extremely dramatic and surprising compared to the conventional methods of treatment that usually take many weeks or months to heal with or without permanent scars left behind. Furthermore, no adverse effects were found in all the studies (Examples I to IV).

Accordingly, the present invention provides an extremely effective, efficacious, simple, rapid, novel, safe, inexpensive method for treating both acne and warts by topically applying an effective amount of one or more polyvalent metal compounds in a suitable dosage form to the area of lesion of the acne or warts. Extremely rapid healing without any side effects and without any scar left behind is in most dramatic contrast with the conventional treatment methods discussed above.

In view of the early success for treating aphthous ulcers and herpes simplex described in PCT International Patent Application No. PCT/US02/18223, the present invention may also be applied to effectively treat other superficial skin diseases caused by other microorganisms including viruses, fungi and yeasts; one such disease is rosacea which is often treated topically using similar drugs as for acne, and requires five to eight weeks of treatment for significant response.

The present invention also provides a very surprising and highly effective method for preventing and minimization of scar formation as well as for rapid healing or sloughing of the scar once formed in any skin lesions caused by a disease such as acne and warts or caused following drug treatment, laser treatment, cryotherapy and surgery ("Current Medical Diagnosis and Treatment" by L. M. Tierney, Jr. et al., Lange Medical Books, NY 2004, pp. 111-113 and 123-125; "Andrews' Diseases of the Skin, Clinical Pharmacology" by R. B. Odom et al., Philadelphia, 2000, pp. 16, 284-306 and 509-519) by a topical application to the area of the scar containing an effective amount of one or more polyvalent metal compounds in a suitable dosage form.

DETAILED DESCRIPTION OF THE INVENTION

As used herein, the word "treatment" or "treating" includes ameliorating the symptoms of, curing or healing, and preventing the development of a given disease such as acne and warts. The phrase "effective amount" refers to that amount of a compound which is sufficient to effect treatment when administered to a mammal in need of such treatment or prevention. The word "prevention" refers to prophylaxis. The word "scar" refers to a mark left on the skin after a wound, burn, ulcer, pustule, lesion, etc. has healed. The words "healing or sloughing" as they relate to scar provide regenerating a new skin tissue to replace the scarred tissue.

As used herein, the phrase "polyvalent metal compound" refers to any organic or inorganic polyvalent compound that has the beneficial therapeutic properties described herein. Polyvalent metal compounds include, but are not limited to, aluminum compounds, magnesium compounds, zinc compounds, calcium compounds, bismuth compounds, titanium compounds, copper compounds, manganese compounds, iron compounds, chromium compounds and barium compounds. A polyvalent compound can be an inorganic or organic salt, an oxide or a complex. Ideally the counter ion to a metal or the ligand moiety to a metal is also therapeutically active or can enhance the therapeutic activity of the metal moiety. One such example may be magnesium salicylate since salicylate is known to have an anti-inflammatory property.

Suitable dosage forms of one or more polyvalent metal compounds include, but are not limited to, a liquid solution or mixture with various viscosity, a suspension, a gel, a cream, a lotion, an emulsion, a paste and a medicated bandage or patch. Pure fine powders or diluted fine powders can also be applied to the open lesion area. The method to prepare a dosage form is based on the standard principles and methods described in various pharmaceutical literature.

Virtually all of the polyvalent metal compounds described below are listed in standard references ("Martindale, The Extra Pharmacopoeia", edited by J. E. F. Reynolds, The Pharmaceutical Press, London, 1989; "The Merck Index", Merck & Co., Inc., Whitehouse Station, N.J., 2001).

In one embodiment of the invention, the therapeutically effective compound is selected from the group consisting of bismuth subsalicylate, bismuth chloride, bismuth oxide, bismuth subcarbonate, bismuth subgallate, bismuth subnitrate, bismuth phosphate, bismuth aluminate, bismuth salicylate, bismuth tribromophenate, bismuth dipropylacetate, bismuth citrate, bismuth subcitrate, bismuth ascorbate, bismuth subcarbonate, bismuth tartrate, and colloidal bismuth subcitrate.

In another embodiment of the invention, the therapeutically effective compound is selected from the group consisting of zinc sulfate, zinc acetate, zinc gluconate, zinc chloride, zinc carbonate, zinc oxide, zinc oleate, zinc stearate, zinc propionate, zinc salicylate, and zinc undecenoate.

In another embodiment of the invention, the therapeutically effective compound is selected from the group consisting of magnesium acetate, magnesium ascorbate, magnesium carbonate, magnesium chloride, magnesium citrate, magnesium stearate, magnesium gluconate, magnesium hydroxide, magnesium salicylate, magnesium sulfate, magnesium lactate, and magnesium oxide.

In another embodiment of the invention, the therapeutically effective compound is selected from the group consisting of aluminum acetate, aluminum carbonate, aluminum chloride, aluminum potassium sulfate, aluminum glycinate, aluminum hydroxide, aluminum lactate, aluminum oxide, aluminum subacetate, aluminum sulfate, aluminum salicylate, aluminum ammonium sulfate, and aluminum phosphate.

In another embodiment of the invention, the therapeutically effective compound is selected from the group consisting of calcium acetate, calcium alginate, calcium benzoate, calcium carbonate, calcium chloride, calcium citrate, calcium gluconate, calcium hydroxide, calcium lactate, calcium phosphate, calcium stearate, calcium sulfate, calcium salicylate and calcium oxide.

In another embodiment of the invention, the therapeutically effective compound is selected from the group consisting of copper gluconate, copper salicylate and copper sulfate.

In one embodiment of the invention, the therapeutically effective compound is selected from the group consisting of titanium dioxide, titanium peroxide, titanium salicylate and titanium tannate.

In another embodiment of the invention, the therapeutically effective compound is selected from the group consisting of ferric chloride, ferric citrate, ferric oxide, ferric sulfate, ferrous ascorbate, ferrous carbonate, ferrous sulfate, ferrous gluconate, ferrous fumarate, ferrous glycine, and ferrous lactate.

In another embodiment of the invention, the therapeutically active compound is selected from the group consisting of manganese acetate, manganese benzoate, manganese borate, manganese carbonate, manganese salicylate, manganese bromide, manganese iodide and manganese diiodide.

In another embodiment of the invention, the therapeutically active compound is selected from the group consisting of chromium potassium sulfate, chromium sulfate, chromium trichloride, chromium piconilate and chromium trioxide.

In another embodiment of the invention, the therapeutically active compound is selected from the group of barium sulfate, barium hydroxide, barium chloride, barium carbonate and barium sulphide.

Generally, the concentration of a polyvalent metal compound for the treatment of acne, warts and rosacea and for the prevention of scar formation or for the healing or elimination of the scar formed in a dosage form will be about 0.05% to about 50% by weight. Other embodiments contain about 0.2% to about 40%, about 0.5% to about 30%, or about 1.0% to about 25% by weight of polyvalent metal compounds. An effective amount of one or more polyvalent metal compounds may also be applied daily to vulnerable skin areas for prophylactic purpose in acne management. Also, any compound or compounds that may further enhance the efficacy of the polyvalent compounds in the treatment of acne or warts can also be incorporated into the dosage form. Skin-peeling compounds such as lactic acid, citric acid and salicylic acid may be added to increase the absorption through the skin.

The present invention is illustrated by the following non-limiting examples. The percentages of ingredients are by weight.

EXAMPLE I

An Aqueous Glycerin Solution Containing 10% Aluminum Potassium Sulfate, 8% Magnesium Sulfate and 1% Zinc Gluconate for Acne Treatment The above solution containing about 70% of glycerin was topically applied once to three adults with an inflammatory papular acne on the face. The papule in two adults was found to disappear the following day with no flare-ups in the following weeks. The third adult had the redness and bump of a papule markedly reduced the following day. Without any additional treatment the redness and bump were completely gone after about ten days.

The fourth adult applied the solution to the area of lesion with an inflammatory papule three times a day. The next day there was a dry dark crust (about 0.4 cm in diameter) formed, and no pain was noted upon touch. The crust sloughed off in about four days without any scar left.

The fifth adult applied the solution about twice a day to the lesion after squeezing out the typical pus from a pustular acne. A dry dark crust (about 0.5 cm in diameter) was formed the next day and no pain was noted afterwards. The acne might be considered "healed" on the second day in this adult although it took about one week to have the scar completely sloughed off; this kind of rapid healing without scarring also occurred in a sixth subject.

EXAMPLE II

A Glycerin Solution Containing 10% Aluminum Potassium Sulfate and 10% Magnesium Sulfate for Treatment of Acne The above solution was applied once prior to bedtime to each of the four small inflammatory papular acnes on the forehead of a female adult. The acnes were found to completely disappear the following morning, indicating complete cure in about eight hours just after one treatment. The above solution was simply prepared by dissolving the two metal compounds in glycerin.

EXAMPLE III

A 20% Paste of Aluminum Potassium Sulfate for Acne Treatment

A small amount of a 20% aqueous paste prepared with 5% hydroxypropylmethylcellulose as a thickening agent was applied to the area of acne lesion on the face of a male adult after squeezing out the pus from a pustular acne. On the second day, the area of lesion was dry and the previous redness was much reduced. After two more applications, on the second day, the lesion was found to completely heal without any scar left on the third day.

EXAMPLE IV

A Polyvalent Metal Suspension for Treatment of Warts

A male adult developed a typical wart with bleeding on his right side of the face for a few weeks. A small amount of a suspension containing about 10% aluminum potassium sulfate, 10% magnesium sulfate and 2% zinc acetate in glycerin was applied to the area of lesion and covered with a bandage. The following day a hanging dark brown tissue was removed. The metal suspension was applied three times on that day and the lesion was found to begin to dry and to heal. The suspension was applied two times the following day without a bandage. The area of the lesion got smaller every day and in about one week only a small needle-size bump was present. A 10% aluminum potassium sulfate in glycerin-water mixture was later tried for three days and the lesion was completely healed without any scar left in a few days.

It is to be understood that the above descriptions are intended to be illustrative, and not restrictive. One skilled in the art will be able to ascertain, without anymore routine experimentation, many equivalents to the specific embodiments described herein. This is particularly true with the use of other polyvalent metal compounds since a large variety of salts, oxides or complexes not specifically mentioned in this application can be synthesized or perhaps obtained commercially. These equivalents are intended to be encompassed by the following claims.

What is claimed is:

1. A method for ameliorating acne comprising topically applying a therapeutically effective amount of one or more aluminum compounds selected from the group of aluminum potassium sulfate, and aluminum ammonium sulfate in a pharmaceutically acceptable dosage form to the area of lesion of the acne.

2. A method for ameliorating acne consisting essentially of topically applying a therapeutically effective amount of one or more aluminum compounds selected from the group of aluminum potassium sulfate, and aluminum ammonium sulfate in a pharmaceutically acceptable dosage form to the area of the lesion of the acne, wherein the concentration of the aluminum compound ranges from about 0.05% to about 50% by weight.

3. The method of claim 1, wherein the concentration of the aluminum compound ranges from about 0.05% to about 50% by weight.

4. A method for ameliorating rosacea comprising topically applying a therapeutically effective concentration of one or more aluminum compounds selected from the group consisting of aluminum potassium sulfate, aluminum sulfate, aluminum lactate and aluminum ammonium sulfate in a pharmaceutically acceptable dosage form to the area of lesion of the rosacea.

5. The method of claim 4, wherein the concentration of the aluminum compound ranges from about 0.05% to about 50% by weight.

6. A method for ameliorating rosacea comprising topically applying a therapeutically effective concentration of one or more bismuth compounds selected from the group consisting of bismuth subsalicylate, bismuth subcarbonate, bismuth subgallate, bismuth subsaltrate, bismuth phosphate, bismuth aluminate, bismuth salicylate, bismuth tribromophenate, bismuth dipropylacetate, bismuth citrate, bismuth subcitrate, bismuth ascorbate, bismuth subcarbonate, bismuth tartrate and colloidal bismuth subcitrate in a pharmaceutically acceptable dosage form to the area of lesion of the rosacea.

7. The method of claim 6, wherein the concentration of the bismuth compound ranges from about 0.05% to about 5% by weight.

8. A method for ameliorating warts in human comprising topically applying a therapeutically effective amount of one or more polyvalent metal compounds in a pharmaceutically acceptable dosage form to the area of the lesion of warts, wherein a metal compound is selected from the group consisting of aluminum potassium sulfate aluminum lactate, aluminum ammonium sulfate, bismuth subsalicylate, bismuth chloride, bismuth oxide, bismuth subcarbonate, bismuth subgallate, bismuth subsaltrate, bismuth phosphate, bismuth aluminate, bismuth tribromophenate, bismuth dipropylacetate, bismuth citrate, bismuth subcitrate, bismuth ascorbate, bismuth tartrate and colloidal bismuth subcitrate.

9. The method of claim 8, wherein the concentration of the polyvalent metal compound ranges from about 0.05% to about 50% by weight.

10. A method for ameliorating warts in human consisting essentially of topically applying a therapeutically effective amount of one or more polyvalent metal compounds in a pharmaceutically acceptable dosage form to the area of the lesion of warts, wherein a metal compound is selected from the group consisting of aluminum potassium sulfate, aluminum lactate, aluminum ammonium sulfate, bismuth subsalicylate, bismuth chloride, bismuth oxide, bismuth subcarbonate, bismuth subgallate, bismuth subsaltrate, bismuth phosphate, bismuth aluminate, bismuth tribromophenate, bismuth dipropylacetate, bismuth citrate, bismuth subcitrate, bismuth ascorbate, bismuth tartrate and colloidal bismuth subcitrate, wherein the concentration of the metal compound ranges from about 0.05% to about 50% by weight.

* * * * *